United States Patent
Giese (10) Patent No.: US 10,734,139 B2
(45) Date of Patent: Aug. 4, 2020

(54) FERRULE HAVING IMPROVED GOLD RESERVOIR GEOMETRY FOR IMPLANTABLE MEDICAL DEVICE

(71) Applicant: Cardiac Pacemakers, Inc., St. Paul, MN (US)

(72) Inventor: Troy Anthony Giese, Blaine, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 442 days.

(21) Appl. No.: 15/485,370

(22) Filed: Apr. 12, 2017

(65) Prior Publication Data

US 2017/0294250 A1 Oct. 12, 2017

Related U.S. Application Data

(60) Provisional application No. 62/321,510, filed on Apr. 12, 2016.

(51) Int. Cl.
*H01B 19/00* (2006.01)
*A61N 1/375* (2006.01)

(52) U.S. Cl.
CPC ........... *H01B 19/00* (2013.01); *A61N 1/3754* (2013.01)

(58) Field of Classification Search
CPC .............................. H01B 19/00; A61N 1/3754
See application file for complete search history.

(56) References Cited

U.S. PATENT DOCUMENTS

| 6,349,025 B1 | 2/2002 | Fraley et al. |
| 7,365,960 B2 | 4/2008 | O'Phelan et al. |
| 8,604,341 B2 | 12/2013 | Barry et al. |
| 9,008,779 B2 | 4/2015 | Morioka et al. |
| 9,064,640 B2 | 6/2015 | Brendel et al. |

(Continued)

FOREIGN PATENT DOCUMENTS

| EP | 0004783 A2 | 10/1979 |
| EP | 1484085 A2 | 12/2004 |

(Continued)

OTHER PUBLICATIONS

Jiang, Guangqiang, et al., "Technology Advances and Challenges in Hermetic Packaging for Implantable Medical Devices", Implantable Neural Prostheses 2, Biological and Medical Physics, Biomedical Engineering, (2010), 27-61.

(Continued)

*Primary Examiner* — Christopher Koharski
*Assistant Examiner* — Roland Dinga
(74) *Attorney, Agent, or Firm* — Schwegman Lundberg & Woessner, P.A.

(57) ABSTRACT

A feedthrough assembly and methods of making the feedthrough assembly are shown. A feedthrough assembly including a ferrule disposed about an insulator and having an outer surface and a first aperture defined by an inner surface, wherein the first aperture is sized and shaped to include a reservoir for a braze material, the reservoir including a base, the base having a width sized to accommodate a preform of the braze material, and at least two ledges formed by the inner surface, each ledge having a first surface facing inwardly toward the insulator and a second surface facing upwardly is shown. Methods of making the feedthrough assembly including such a ferrule are shown.

20 Claims, 4 Drawing Sheets

(56) References Cited

U.S. PATENT DOCUMENTS

| | | | |
|---|---|---|---|
| 2005/0092507 A1 | 5/2005 | Marshall et al. | |
| 2005/0197677 A1* | 9/2005 | Stevenson | A61N 1/37 607/36 |
| 2007/0060970 A1 | 3/2007 | Burdon | |
| 2010/0202096 A1 | 8/2010 | Iyer | |
| 2011/0106228 A1 | 5/2011 | Reiterer et al. | |
| 2012/0006576 A1* | 1/2012 | Barry | A61N 1/3754 174/50.6 |
| 2014/0371835 A1* | 12/2014 | Powell | B23K 1/0008 607/137 |
| 2015/0165218 A1* | 6/2015 | Markham | A61N 1/3754 607/116 |
| 2015/0245468 A1* | 8/2015 | Barry | A61N 1/08 174/257 |

FOREIGN PATENT DOCUMENTS

| | | |
|---|---|---|
| EP | 2082780 A2 | 7/2009 |
| EP | 2273518 A2 | 1/2011 |
| WO | WO-2013019739 A1 | 2/2013 |
| WO | WO-2013122947 A2 | 8/2013 |

OTHER PUBLICATIONS

Sherwood, Gregory J., et al., "Capacitive Filter Ferrule for Implantable Medical Device, U.S. Appl. No. 61/598,961, filed Feb. 15, 2012".

* cited by examiner

FERRULE HAVING IMPROVED GOLD RESERVOIR GEOMETRY FOR IMPLANTABLE MEDICAL DEVICE

CLAIM OF PRIORITY

This application claims the benefit of priority under 35 U.S.C. § 119(e) of U.S. Provisional Patent Application Ser. No. 62/321,510, filed on Apr. 12, 2016, which is herein incorporated by reference in its entirety.

BACKGROUND

Implantable medical devices (IMDs) are used to treat many conditions. IMDs devices such as pacemakers and defibrillators include electronics mounted within a housing. The electronics are typically operatively connected to a lead or leads, which can be implanted in or about the heart. The leads implanted in or about the heart can be used to reverse certain life-threatening arrhythmias, or to stimulate contraction of the heart. Electrical energy is applied to the heart via electrodes on the leads to return the heart to normal rhythm.

An electrical feedthrough can be used in an IMD to provide an isolated electrical path from an exterior of the IMD to an interior of a housing. Feedthroughs can be used with housings that are sealed, such as biocompatible, hermetically sealed housings. To preserve internal components, the feedthrough can be leak-resistant. Some feedthroughs are biocompatible and hermetically sealed. Some IMDs using such hermetically sealed feedthroughs can protect implanted electronics from body fluids and can resist undesirable exposure of the patient to materials from inside the housing.

To provide such an electrical feedthrough, a ferrule (or mechanical element) can be disposed through the housing and coupled to the housing. A conduit or member that is able to conduct electricity can extend through the ferrule. An electrical insulator, such as being formed from a ceramic material, can be disposed between the ferrule and the electrically conductive conduit. The conduit and the insulator can have a braze joint therebetween, and the ferrule and the insulator can have a braze joint therebetween, which both hermetically seal the conduit and the ferrule with the insulator. A hermetically sealed, electrical feedthrough configured as such can maintain hermeticity of the housing while allowing an electrical signal to enter or exit the housing.

OVERVIEW

In the manufacture of electrical feedthroughs for IMDs, one or more gold preforms can be used as a precursor to form a braze joint. During manufacture, a first gold preform can be placed in a reservoir in a ferrule between the ferrule and an insulator, such as before reflowing during a braze cycle. A second gold preform can be placed in a space between a conduit and the insulator. Once heated, both of the gold preforms melt to liquid gold. The liquid gold tends to attract to materials that it has a high affinity towards (such as titanium, palladium, and platinum), especially those of which it is in immediate, intimate contact with (e.g., a surface of the ferrule). Since the ferrule can be made of titanium and/or palladium, for example, the liquid gold can tend to remain on the ferrule instead of migrating into a desired gap or region between the ferrule and the insulator in order to form a braze joint. The liquid gold can also wick or migrate along the surface of the ferrule in a direction away from the gap used to form the braze joint.

In forming the braze joint between the ferrule and the insulator, there should be enough gold in the preform to fill the pocket or reservoir when melted and overcome surface tension to bulge and bridge to the insulator. Particularly in feedthrough designs that include a flush insulator or a recessed insulator, rather than a protruding insulator, more gold can help ensure a sufficient supply for a hermetic seal to be formed. Flush or recessed designs can use approximately twice as much gold in preforms as designs including protruding insulators.

The inventor has recognized, among other things, that it can be beneficial to reduce the amount of gold needed in the gold preform used during the brazing process in forming a hermetically-sealed feedthrough assembly, such as having a flush or recessed insulator. The present subject matter can help provide a solution to this problem by improving the geometry of the gold reservoir in order reduce the amount of gold used in the preform.

During the brazing process, once the insulator wets with gold, the gold can be pulled or wicked into a braze gap located between the ferrule and insulator via surface tension or capillary action, and the braze joint can be formed therebetween. There can be left-over or "wasted" gold still remaining in the reservoir, which does not get pulled or wicked into the braze gap. Liquid gold can also wick along the surface of the ferrule in a direction away from the braze gap, which can also result in wasted gold.

The inventor has also recognized that the amount of gold needed in the preform may also be reduced by avoiding or inhibiting the wicking or migration of liquid gold along the surface of a ferrule in the direction away from the braze joint gap. The present subject matter can help provide a solution to this problem, such as by disrupting the wetting forces of the liquid gold as it moves away from the braze gap. Disruption of the wetting forces can be accomplished by varying the geometry of the reservoir, such as described further herein.

One way in which the geometry can disrupt the wetting forces can be by including sharp corners or ledges in an inner surface of the reservoir in the direction away from the braze gap. Wetting forces were found to drop off significantly on the inner surface of the reservoir when sharp ledges or corners each having two surfaces that were about 270 degrees apart, or that were substantially orthogonal to one another, were included in the inner surface of the ferrule. Including a second sharp ledge radially outward from a first sharp ledge can stop liquid gold, for example, from moving beyond that second, sharp ledge.

Another way in which the geometry can disrupt the wetting forces is by having the first ledge, which is located closest inwardly to the insulator, have a height that is low enough, compared to the height of the preform, to allow a significant amount of the liquid gold to bulge upon melting prior to contacting and wetting the surface of the ferrule in a direction outward from the braze gap. The gold can similarly bulge inwardly toward the insulator and can begin to wet the insulator surface prior to wetting above the inner surface of the reservoir. As a result, more liquid gold can be drawn toward the braze gap rather than drawn away and wasted.

The inventor has also recognized that during the brazing process, gold can be wasted by being splashed onto other surfaces, particularly onto an upper surface of the insulator. The present subject matter can help provide a solution to this problem, such as by having an upper surface of the gold preform below the upper surface of the insulator, in order to prevent gold from splashing on the upper surface of the insulator.

A feedthrough assembly and methods of making the feedthrough assembly are shown. A feedthrough assembly including a ferrule disposed about an insulator and having an outer surface and a first aperture defined by an inner surface, wherein the first aperture is sized and shaped to include a reservoir for a braze material, the reservoir including a base, the base having a width sized to accommodate a preform of the braze material, and at least two ledges formed by the inner surface, each ledge having a first surface facing inwardly toward the insulator and a second surface facing upwardly is shown. Methods of making the feedthrough assembly including such a ferrule are shown.

This section is intended to provide an overview of subject matter of the patent application. It is not intended to provide an exclusive or exhaustive explanation of the invention. The detailed description is included to provide further information about the patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
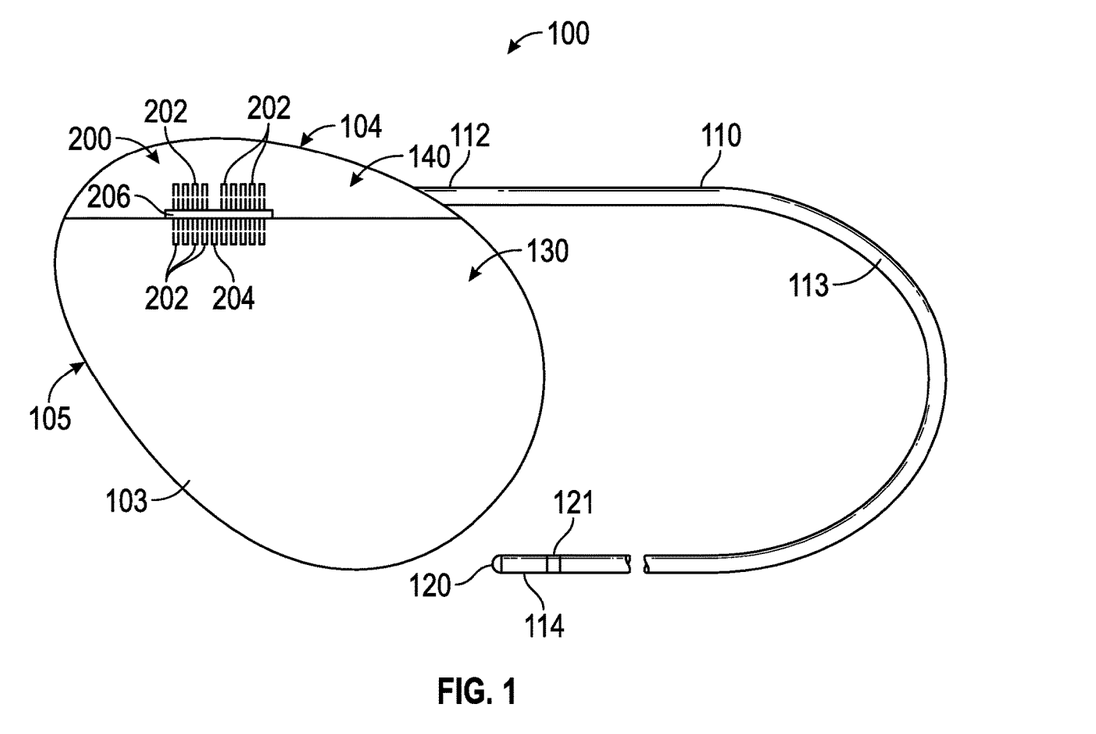
FIG. 1 shows an example of an implantable medical device.

FIG. 1 shows an example of an implantable medical device (IMD) 100. Device 100 can include an electronics unit, such as a pulse generator 105, and at least one lead 110. The pulse generator 105 can be generally implanted into a subcutaneous pocket made in an upper pectoral region of a patient. Alternatively, the pulse generator 105 can be placed in a subcutaneous or submuscular pocket made in an abdomen, or in other locations. Pulse generator 105 can generally include a hermetically sealed housing 103 and a header 104. The housing 103 can be hermetically sealed and formed with an exterior of biocompatible and biostable material (e.g., titanium, biocompatible coating) protecting the interior of the housing 103 from the bodily fluids of a patient that are outside the housing 103. Header 104 can be mechanically and electrically coupled to housing 103. Pulse generator 105 can include a power supply such as a battery, a capacitor, and other components housed in housing 103. The pulse generator 105 can also include circuitry, such as a microprocessor, to provide processing, evaluation, or to determine and deliver electrical shocks or pulses of different energy levels or timing for defibrillation, cardioversion, or pacing to a heart such as in response to cardiac arrhythmia including fibrillation, tachycardia, heart failure, and bradycardia.

Lead 110 can include a lead body 113 having a proximal end 112, such as where the lead can be coupled to header 104 of pulse generator 105. The lead 110 can extend to a distal end 114, which can be coupled with a portion of a heart, when implanted. The distal end 114 of the lead 110 can include one or more electrodes 120, 121. In an example, one or more electrodes can be located medially or at other locations along the lead. At least one electrical conductor can be disposed within the lead 110, such as to extend from the proximal end 112 to at least one respective electrode(s) 120, 121. The electrical conductors can carry electrical current and pulses between the pulse generator 105 and the electrode(s) 120, 121.

In an example, IMD 100 can be suitable for use as or with one or more implantable electrical stimulators, such as, but not limited to, pulse generators, neuro-stimulators, skeletal stimulators, central nervous system stimulators, or stimulators for the treatment of pain. The device can also be utilized as a sensor or a receiver, or both. The electrodes can be used, for sensing, pacing, or shocking, for example.

An example of a feedthrough assembly 200 is schematically shown in FIG. 1. The feedthrough assembly 200 can be attached to a hole in the housing 103 and can be attached so that the housing 103 is hermetically sealed. The feedthrough assembly 200 can facilitate electric transmission through the housing 103, from the interior of the housing 103 to the exterior of the housing 103, and vice versa. The feedthrough assembly 200 can, for example, include a plurality of feedthrough wires 202 or can be mounted within and extending through an insulator (not visible in FIG. 1) of the feedthrough assembly 200 from an interior 130 of the housing 103 to an exterior 140 of the housing 103. The feedthrough assembly 200 can further include a ground wire 204 that can be directly attached to a ferrule 206 of the feedthrough assembly 200. The ground wire 204 need not pass through or alongside the insulator of the feedthrough assembly 200. Instead, in an example, the ground wire 204 can be located and attached to electronics on the interior side 130 of the housing 103 and need not be exposed on the exterior side 140 of the housing 103.

The feedthrough assembly 200, as well as the remainder of the exterior of the housing 103, can be hermetically sealed, biocompatible, and biostable such as to prevent leakage of bodily fluids to the interior of the housing 103, as well as to prevent leakage from the interior of the housing 103 into the body during the usable life of the IMD 100. The feedthrough assembly 200 can be hermetically sealed and can remain hermetically sealed when implanted in the body, such as having long-term biostability on the order of years, such as at least a year, five years, ten years, twenty years, or more.

Although described herein with respect to particular IMDs, it should be understood that the concepts disclosed herein may be utilized in conjunction with a wide range of IMDs, such as pacemakers, implantable cardioverter-defibrillators, sensors, cardiac contractility modulators, cardioverters, drug-administering devices, diagnostic recorders, cochlear implants, or other devices. Devices other than IMDs may also benefit from the concepts disclosed herein.

Figure 2:
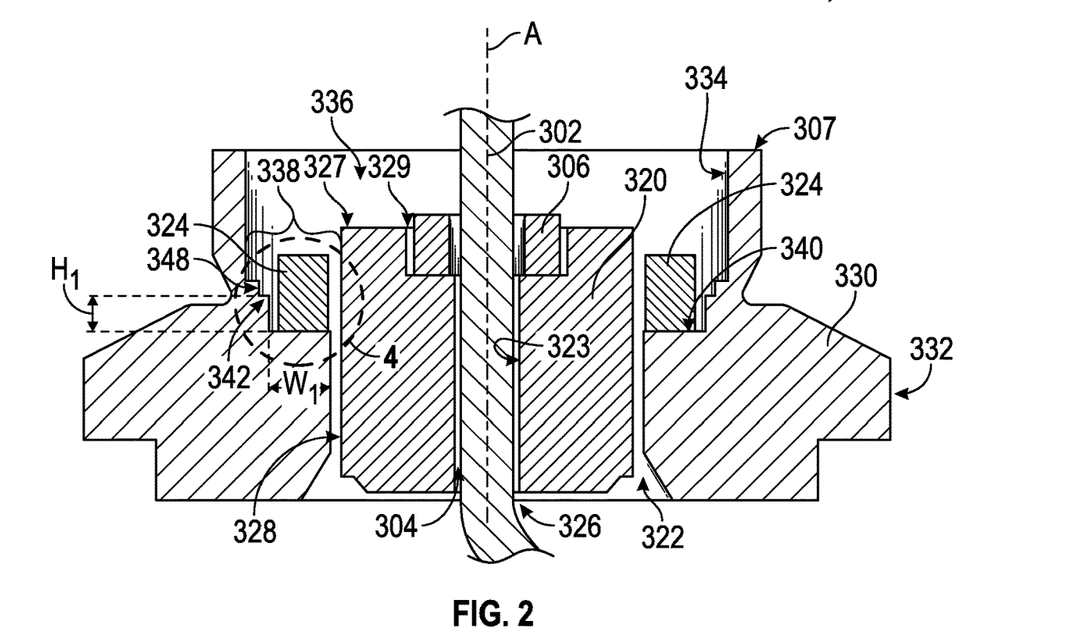
FIG. 2 shows an example of a cross-section of a feedthrough assembly prior to undergoing a brazing process.
Figure 3:
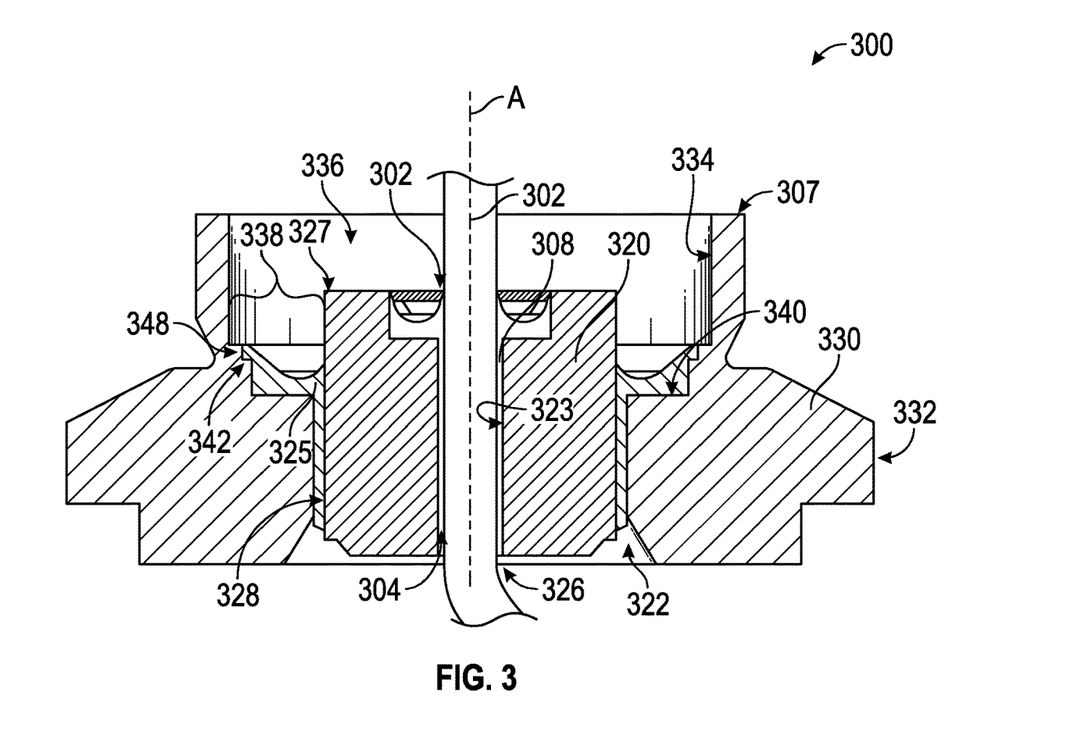
FIG. 3 shows an example of the cross-section of the feedthrough assembly of FIG. 2 after undergoing the brazing process.

FIGS. 2 and 3 show cross-sections of an example of a feedthrough assembly 300. The feedthrough assembly 300 in FIG. 2 is shown before undergoing a brazing process, and FIG. 3 shows the feedthrough assembly 300 after undergoing the brazing process. The feedthrough assembly 300 can include an electrically conductive member or conduit 302 (e.g., a pin or wire) extending through, or surrounded by, an electrical insulator 320. Insulator 320 can be disposed about the conductive member 302, and before undergoing a brazing process, can be separated from conductive member 302 by an insulator-conductive member braze gap or region 304 (such as shown in FIG. 2). A first preform 306 can include a braze material, such as gold, and can be located adjacent the insulator-conductive member braze gap 304 (FIG. 2). After the brazing process, and melting of the first preform 306, the insulator-conductive member braze gap or region 304 can be filled with the braze material 308 from first preform 304 that melted and migrated or was wicked into the insulator-conductive member braze gap 304, such as via surface tension or capillary action (such as shown in FIG. 3). Insulator 320 is shown surrounded by or disposed within a ferrule 330. Ferrule 330 can be brazed to insulator 320 and before brazing, therefore, can be separated from insulator 320 by a ferrule-insulator braze gap or region 322 (as shown in FIG. 2). A second preform 324 comprising a braze material, such as gold, can be located adjacent the ferrule-insulator braze gap 322 (FIG. 2). After undergoing a brazing process, ferrule-insulator braze gap 322 can be filled with a braze material 325 from second preform 324 that was liquefied and migrated or wicked into the ferrule-insulator braze gap 322, such as via surface tension or capillary action (such as shown in FIG. 3). The brazing operations may occur at the same time for each braze material; that is, braze gaps 304 and 322 could be filled at the same time. If, however, the first and second preforms 306, 324 are made of two different materials, for example, it is possible that the two materials may not melt at the same temperature or at the same time during the brazing process.

A conductive path can be provided through feedthrough assembly 300 by conductive member 302. Although feedthrough assembly 300 is shown with one conductive member 302, the feedthrough assembly 300 may include a plurality of electrically conductive members or elements 302. Conductive member 302 can be formed of one or more materials such as stainless steel, cobalt-chrome, nickel-titanium, niobium, titanium, niobium-titanium alloy, titanium-6Al-4V alloy, titanium-vanadium alloy, platinum, iridium, molybdenum, zirconium, tantalum, vanadium, tungsten, palladium, nickel super alloy, nickel-chromium-cobalt-molybdenum alloy, and alloys, mixtures, and one or more combinations thereof.

While FIGS. 2 and 3 show a cross-section of a cylindrically-shaped insulator 320 disposed about conductive member 302, other shapes can be used. Insulator 320 can include a single aperture 326 through which conductive member 302 extends. However, an insulator portion in another example can include a plurality of holes extending through the insulator, such as to accommodate a plurality of conductive members.

FIGS. 2 and 3 show a central, longitudinal axis A that can be defined so as to extend generally vertically through aperture 326 of insulator 320. Terms included herein that reference direction and position with regard to features of feedthrough assembly 300 are relative to the illustrated segment of the axis A. Such terms include, but are not limited to, upwardly, upper, outwardly, outward, inward, or inwardly, etc.

Insulator 320 can include an upper surface 327, an outwardly-facing surface 328, and an inwardly-facing surface 323. Insulator 320 can also include a recess or holding area 329 in the upper surface 327 such as for locating or maintaining therein the first preform 306 before brazing (FIG. 2). The recess 329 can be adjacent and connected to the insulator-conductive member braze gap 304, such that the first preform 306 can melt and the braze material 308 can flow or otherwise move, such as including via surface tension capillary action, into the insulator-conductive member braze gap 304, such as to form a braze joint, and hermetically seal the conductive member 302 to the insulator 320.

Feedthrough assembly 300 is shown with a recessed insulator, which means that the upper surface 327 of the insulator 320 does not extend to a top, or upper surface, 307 of feedthrough assembly 300, but instead is recessed within feedthrough assembly 300. The feedthrough assemblies described herein can include either a recessed insulator 320, such as that shown in FIGS. 2 and 3, or a flush insulator (not shown) in which an upper surface of such an insulator can extend to a top, or upper surface of a feedthrough assembly. Although the described feedthrough assemblies 300 (FIGS. 2-4) and 400 (FIG. 5, discussed below) are contemplated for use in feedthrough assembly designs including recessed or flush insulators, it is also contemplated that the feedthrough assemblies described may include a protruding insulator or an insulator having other configurations.

Insulator 320 can be formed from a material such as can include one or more of an inorganic ceramic material (e.g., sapphire), a glass or a ceramic-containing material (e.g., diamond, ruby, aluminum oxide, and zinc oxide), or an electrically insulative material. Insulator 320 can also be formed from or include one or more of a liquid-phase sintered ceramic, a co-fired ceramic, a high-temperature glass, or one or more combinations thereof. Insulator 320 is not limited to any particular configuration for use in feedthrough assembly 300, but can generally be configured to accommodate one or more electrically conductive members 302.

Ferrule 330 can be disposed about insulator 320. Ferrule 330 can include a ferrule outer surface 332 and a ferrule lumen or inner surface 334 that can define an aperture 336. The aperture 336 can be sized and shaped to include a reservoir 338 such as for a braze material. The reservoir 338 can be sized and shaped to accommodate a second preform 324 before brazing (such as shown in FIG. 2), and to allow for flow of liquefied braze material during or resulting from brazing (as in FIG. 3). The reservoir 338 can be generally located radially outward from the outwardly-facing surface 328 of insulator 320. The reservoir 338 can include a base 340, which can have a width W1 that can be sized and shaped to accommodate a preform of braze material, such as the second preform 324 (such as shown in FIG. 2). The reservoir 338 can also include at least two ledges that can be formed by the inner surface 334 of the ferrule 330. The example of FIGS. 2 and 3 can include a first ledge 342 and a second ledge 348, however one or more additional ledges can be included, such as a third ledge, fourth ledge, or fifth ledge, etc. The first ledge 342 of the at least two ledges can be located radially inward toward the insulator 320 from the second ledge 348. The reservoir 338 can concentrically surround the insulator 320 and the at least two ledges 342, 348 can extend around the insulator 320. The at least two ledges 342, 348 can be offset from each other along axis A of the feedthrough assembly 300. Each ledge 342, 348 can include a first surface facing inwardly toward the insulator 320 and a second surface facing upwardly.

Figure 4:
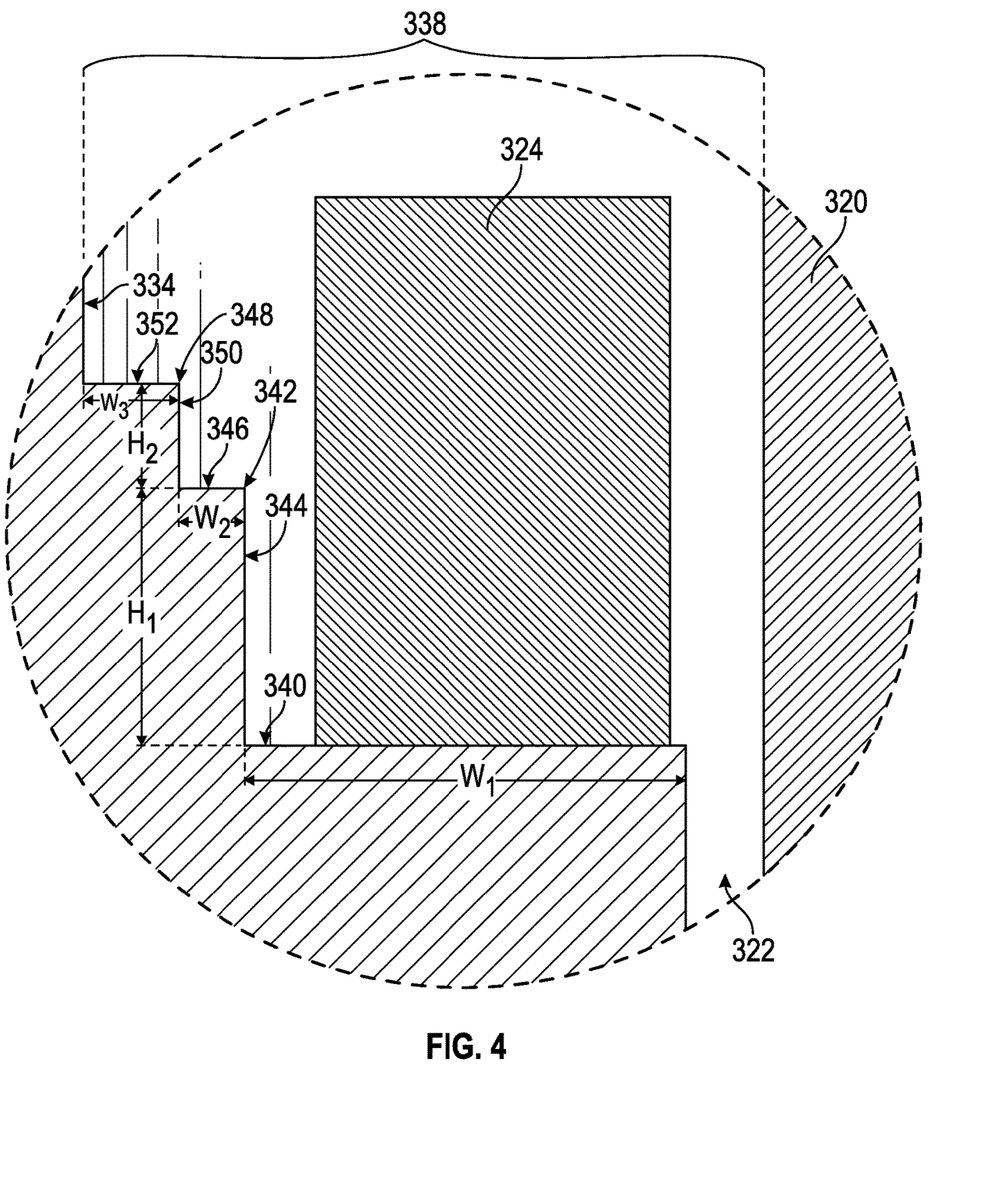
FIG. 4 shows an example of a close-up view of a portion of FIG. 2 (indicated by dashed circle labelled 4).

FIG. 4 is an example of a close-up view of a portion of FIG. 2, as indicated by a dashed circle labelled as 4 in FIG. 2. The close-up view shows the portion of FIG. 2 particularly including an example of the reservoir 338. First ledge 342 is shown including a first surface 344 facing inwardly toward the insulator 320 and a second surface 346 facing upwardly (or extending horizontally). Second ledge 348 is shown including a first surface 350 facing inwardly toward the insulator 320 and a second surface 352 facing upwardly (or extending horizontally). In FIG. 4, the first surface 344 of the first ledge 342 can extend upwardly from the base 340 of the reservoir 338 generally orthogonally, and the second surface 346 of the first ledge 342 can meet the first surface 344 of the first ledge 342 generally orthogonally, and can extend outwardly away (e.g., radially outwardly) from the insulator 320. The first surface 350 of the second ledge 348 can extend upwardly from the second surface 346 of the first ledge 342 generally orthogonally, and the second surface 352 of the second ledge 348 can meet the first surface 350 of the second ledge 348 generally orthogonally and can extend outwardly away (e.g., radially outwardly) from the insulator 320.

The terms "orthogonal" and "orthogonally" mean intersecting or lying at or near right angles. The term "generally orthogonally" is contemplated to include angles that deviate from 90 degrees. For example, the first surfaces 344, 350 and second surfaces 346, 352 of each of the first ledge 342 and second ledge 348 (FIG. 4), respectively, are described as meeting generally orthogonally, however, the angles may or may not be a right angle and can meet at an angle greater than or less than 90 degrees.

Referring back to FIG. 3, the figure shows the feedthrough assembly 300 after undergoing the brazing process. Melted gold 325 (that resulted from melting of the second preform 324, as shown in FIG. 2) is shown as filling the ferrule-insulator braze gap 322, thus forming a hermetic seal. There can be gold still remaining in the reservoir 338, such as shown, which was not pulled or wicked into the ferrule-insulator braze gap or joint 322. Since liquid gold has a high affinity towards titanium and palladium, and the ferrule 330 can be made of such materials, for example. Some of the liquid gold 325 can wick or migrate along its surface in a direction away from ferrule-insulator braze gap 322. As shown, the inner surface 334 of the ferrule 330, in the area of the reservoir 338, can include sharp corners or ledges 342, 348. Such sharp corners or ledges can disrupt the wetting forces of the liquid gold as it moves along the inner surface 334 of the ferrule 330 away from the ferrule-insulator braze gap 322. Sharp corners or ledges having two surfaces that are about 270 degrees apart, or that are substantially orthogonal to one another are effective in inhibiting migration of liquid gold along the inner surface 334 of ferrule 330 in a direction radially outward from insulator 320. In particular, migration or wicking of the liquid gold 325 past the sharp corner of the second ledge 348, where the first surface 350 and the second surface 352 of the second ledge 348 meet, can be inhibited. Although two ledges are discussed and shown herein, more than two ledges may be included in the inner surface 334 of the ferrule 330 in the area of the reservoir 338.

In combination with, or alternatively to, the presence of the sharp corners or ledges described above, the height H1 of the first ledge 342 can also affect the migration of liquid gold 325 away from the ferrule-insulator braze gap 322. The height H1 of the first ledge 342, which is located closest inwardly to the insulator 320, can have a height that is low enough, compared to the height of the preform 324, such as to allow some of the liquid gold 325 to bulge upon melting before contacting and wetting the surface 334 of the ferrule 330 in a direction outward from the braze joint gap 322. The gold can similarly bulge inwardly toward the insulator 320 and can begin to wet the outer surface 328 of the insulator 320 before wetting the inner surface 334 of the reservoir 338. As a result, more liquid gold 325 can be drawn toward the ferrule-insulator braze gap 322 rather than drawn away and wasted. The preform 324 can have a height that is about 175-225% of the height H1 of the first ledge 342, although other comparable heights are contemplated. For example, the height of the preform 324 can be about 0.015 inches (0.38 mm) while the height H1 of the first ledge 342 can be about 0.007 inches (0.1778 mm). Other heights of the preform 324 and the first ledge 342 are contemplated, however.

In addition, the height H1 of the first ledge 342 can also, or alternatively, be selected relating to the width W1 of base 340. The ratio of H1 to W1 can also affect whether or not the preform 324, upon heating, can bulge inwardly toward the insulator 320 and begin to wet the outer surface 328 of the insulator 320 before wetting the inner surface 334 of the reservoir 338. The height H1 of first ledge 342 (or length of first surface 344) can be selected such that a ratio of the height H1 of the first ledge 342 to the width W1 of the base 340 of the reservoir 338 can fall within a range of 0.45 to 0.75.

The width W2 of the first ledge 342 and the height H2 of the second ledge 348 (each individually or together) can also affect the migration of liquid gold 325 away from the ferrule-insulator braze gap 322. The purpose of the first ledge 342 can be to capture the braze material that splashes above the first surface 344. Once the braze material wets the horizontal surface 346 of the first ledge 342, it will wet outwardly to the first surface 350 of the second ledge 348 and may continue until it reaches near or to the top of the second ledge 348. Optimizing these ledge lengths reduces the amount of braze material being removed from the braze gap 322. The width W2 of first ledge 342 and the height H2 of second ledge 348 can be selected to avoid wetting of the braze material beyond the first surface 350 of the second ledge 348. Ideal values for the ratio of width W2 to width W1 can fall within the range of 0.10 to 0.35 and the ratio of the height H2 to width W1 can fall within the range of 0.15 to 0.50. The width W3 of the second ledge 348 can be in a range starting from 0.001 inches and going up to any width that is suitable. The braze material should not move onto the second surface 352 of the second ledge 348, and should not move past the corner of the second ledge where the first surface 350 and second surface 352 meet. The width W3, therefore, can be any suitable width, as the braze material should not contact the second surface 352 of the second ledge 348.

Ferrule 330 can be formed of an electrically conductive material, such as a metallic material including one or more of stainless steel, titanium, niobium, platinum, molybdenum, tantalum, zirconium, vanadium, tungsten, iridium, palladium, nickel super alloy, alloys, mixtures, or one or more combinations thereof. Ferrule 330 can include or can be composed of an electrically-conductive biocompatible material. Ferrule 330 can be machined from a block of suitable material, stamped from a suitable material, such as by progressive-die stamping, or can be formed by any other suitable method.

Braze or brazing material can form a hermetic seal between the insulator 320 and the ferrule 330, and between the conductive element 302 and the insulator 320. Examples of suitable braze materials can include high purity gold, one or more gold alloys containing silver, copper, tin, and/or zinc, or the like. The braze material can be reinforced with one or more of oxide, carbide, or nitride particles of refractory metals such as molybdenum, tungsten, hafnium, niobium, and zirconium.

The first preform 306 and second preform 324 can be cylindrically-shaped and sized to fit within recess 329 and reservoir 338, respectively. However, other shapes and sizes of preform can be used, the selection of which can depend on the configuration of the feedthrough assembly.

A height of the second preform 324 can be selected such as to permit the second preform 324, when placed in the base 340 of the reservoir 338, to be located below the upper surface 327 of the insulator 320. The height of the second preform 324 being below the upper surface 327 of the insulator 320 can result in a reduction or inhibition of braze material being splashed on the upper surface 327 of the insulator 320.

Figure 5:
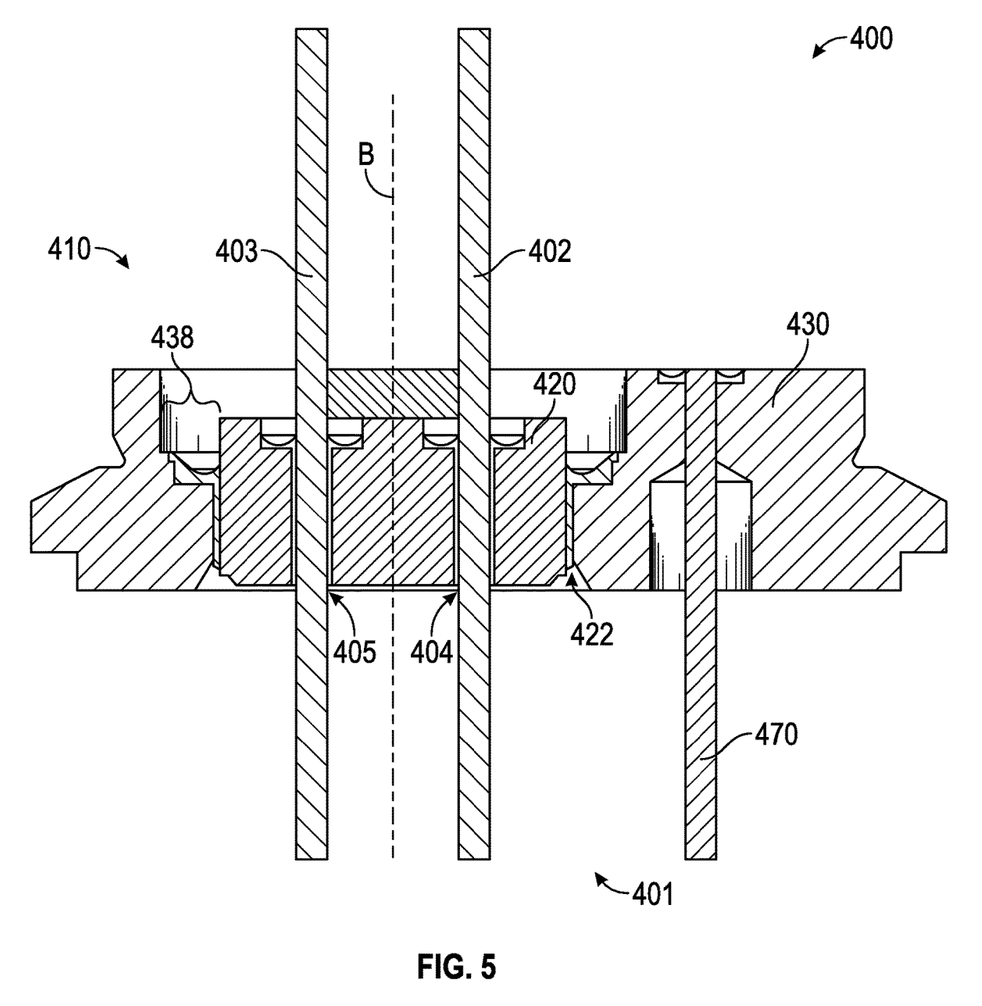
FIG. 5 shows an example of a cross-section of a feedthrough assembly after undergoing a brazing process.

FIG. 5 shows a central, longitudinal axis B that can be defined so as to extend generally vertically through an electrical insulator 420. Terms included herein that reference direction and position with regard to features of feedthrough assembly 400 are relative to the shown segment of axis B. Such terms include, but are not limited to, upwardly, upper, outwardly, outward, inward, or inwardly, etc.

FIG. 5 shows a cross-section of an example of a feedthrough assembly 400. The feedthrough assembly 400 is shown after undergoing a brazing process. The feedthrough assembly 400 can include two or another number of electrically conductive members or conduits 402, 403 extending generally parallel to axis B and through, or surrounded by, the insulator 420. Insulator 420 can be disposed about both conductive members 402, 403, and can be hermetically sealed to conductive members 402, 403 such as at a first insulator-conductive element braze gap or region 404 and a second insulator conductive member braze gap or region 405, respectively, which are shown filled with a braze material. Insulator 420 is shown surrounded by or disposed within a ferrule 430. Ferrule 430 can be brazed (and hermetically sealed) to insulator 420 at a ferrule-insulator braze gap or region 422. Features of the ferrule 430 can be like those described with regard to feedthrough assembly 300 shown in FIGS. 2-4. The example of a feedthrough assembly 400 shows that a plurality of conductive members, such as 402, 403, can be mounted within and extend through the insulator 420 from an interior side 401 of the feedthrough assembly 400 to an exterior side 410 of the feedthrough assembly 400. The conductive members 402, 403 can be hermetically sealed or connected to the insulator 420 separately using gold-brazed joints, for example.

A ground wire 470 (such as seen in FIG. 5) can optionally be located along feedthrough assembly 400 with respect to the plurality of feedthrough wires or conductive member 402, 403. The ground wire 470 need not pass through or alongside the insulator 420. The ground wire 470 can be located on the interior side 401 and need not be exposed on the exterior side 410 and thus does not require hermetic connection. By not allowing the ground wire 470 to pass through or alongside the insulator 420, the present feedthrough assembly can have one less potential leak path that could compromise the hermetic seal of the feedthrough assembly 400. The fewer number of holes or other leak paths through the insulator 420 can provide for a more robust hermetic seal.

The feedthrough assembly 300, such as shown in FIGS. 2-4, can be manufactured such as described in the following example. Ferrule 330 can be formed using a suitable method, such as being machined from a block of suitable material (e.g., titanium). The ferrule 330 can be machined to have specifications, geometries, features, etc., such as those described herein with regard to ferrule 330, although other embodiments are contemplated. For example, ferrule 330 can be machined to include an outer surface 332 and a first aperture 336 defined by an inner surface 334, wherein the first aperture 336 is sized and shaped to include a reservoir 338 for a braze material. The reservoir 338 can include a base 340 having a width W1 sized and shaped to accommodate a preform 324 comprising the braze material, and at least two ledges 342, 348 formed by the inner surface 334. Each ledge 342, 348 can have a first surface 344, 350, respectively, facing inwardly toward the insulator 320 and a second surface 346, 352, respectively, facing upwardly, and a first ledge 342 of the at least two ledges can be located radially inward toward the insulator 320 from a second ledge 348.

An electrical insulator 320 can be provided or inserted through the first aperture 336. The insulator 320 can have a first surface 328 separated from the inner surface 334 of the ferrule 330 by the reservoir 338 and a second, inwardly facing surface 323 defining a second aperture 326. A first braze region (ferrule-insulator braze gap 322) can also separate the insulator 320 from the inner surface 334.

One or more conductive elements can be inserted through the insulator. As shown in the example in FIGS. 2-4, however, only one conductive member 302 is provided in the second aperture 326, with the conductive element 302 being spaced from the insulator 320 by a second braze region 304. A plurality of conductive members can be used, however, in some examples.

A preform 324 can include the braze material and can be provided to the base 340 of the reservoir 338 and another preform 306 can include the braze material and can be provided adjacent the second braze region 304. The feedthrough assembly 300 can be heated to melt the first and second preforms 324, 306 and braze the ferrule 330 to the insulator 320 in the first braze region 322 and to braze the conductive element 302 to the insulator 320 in the second braze region 304.

In the method, a combination of a measure of an angle at which the first surface 344, 350 and the second surface 346, 352 of each of the first and second ledges 342, 348, respectively, meet, and a height H1, H2 of the first surface 344, 350 of each of the first and second ledges 342, 348, respectively, can be selected in order to avoid wetting of the gold beyond the first surface 350 of the second ledge 348 (i.e., or beyond where the first surface 350 and the second surface 352 meet at a corner or edge of the second ledge 348). A height of the preform 324 can be selected such that the preform 324, when placed in the base 340 of the reservoir 338, can be located below the upper surface 327 of the insulator 320. A height H1 of the first surface 344 of the first ledge 342 can be selected such that a ratio of the height H1 of the first surface 344 of the first ledge 342 to the width W1 of the base 340 of the reservoir 338 falls within a range of 0.45 to 0.75. The width W3 of the second ledge 348 (or of surface 352) can be in a range from 0.001 inches and up.

In the method, gold can be used as the braze material and titanium can be used to form the ferrule. These materials can be used due to the associated biocompatible properties or relative melting temperatures. In some embodiments, side walls of the insulator can also be coated (e.g., by a variety of potential methods, such as physical vapor deposition, sputtering, electron beam evaporation, plating, chemical vapor deposition) with a metal, such as niobium, titanium, molybdenum, or other biocompatible materials, or facilitate joining between the insulator and the ferrule. The coat of metal may facilitate adhesion and brazing of a gold preform to join the insulator and the ferrule. In other examples, preforms and ferrules can be formed from different materials or combinations of materials.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

VARIOUS NOTES & EXAMPLES

To better illustrate the assemblies and methods disclosed herein, a non-limiting list of embodiments is provided here:

Example 1 includes a feedthrough assembly, including: at least one electrically conductive member; an electrical insulator disposed about the at least one conductive member; and a ferrule disposed about the insulator and having an outer surface and a first aperture defined by an inner surface, wherein the first aperture is sized and shaped to include a reservoir for a braze material, the reservoir including a base, the base having a width sized to accommodate a preform of the braze material, and at least two ledges formed by the inner surface, each ledge having a first surface facing inwardly toward the insulator and a second surface facing upwardly; wherein the insulator is separated from the ferrule by a first braze region that is connected to the base of the reservoir, and the insulator is separated from the conductive member by a second braze region, each braze region is configured to be filled with the braze material that hermetically seals the feedthrough assembly.

Example 2 includes the feedthrough assembly of example 1, wherein the ferrule comprises titanium and the braze material comprises gold, and a first ledge of the at least two ledges is located radially inward toward the insulator from a second ledge, and a combination of a measure of an angle at which the first surface and the second surface of each of the first and second ledges meet and a height of the first surface of the first ledge, is selected in order to avoid wetting of the gold beyond the first surface of the second ledge.

Example 3 includes the feedthrough assembly of any one of examples 1-2, wherein the first surface and the second surface of each of the at least two ledges meet orthogonally.

Example 4 includes the feedthrough assembly of any one of examples 1-3, wherein the first surface of a first ledge of the at least two ledges extends upwardly from the base of the reservoir, the second surface of the first ledge meets the first surface of the first ledge orthogonally and extends outwardly away from the insulator, the first surface of a second ledge extends upwardly from the second surface of the first ledge, and the second surface of the second ledge meets the first surface of the second ledge orthogonally and extends outwardly away from the insulator.

Example 5 includes the feedthrough assembly of any one of examples 1-4, wherein the reservoir concentrically surrounds the insulator and the at least two ledges extend around the insulator.

Example 6 includes the feedthrough assembly of any one of examples 1-5, wherein the feedthrough assembly has a longitudinal axis and the at least two ledges are offset from each other along the longitudinal axis.

Example 7 includes the feedthrough assembly of any one of examples 1-6, wherein a first ledge of the at least two ledges is located radially inward toward the insulator from a second ledge.

Example 8 includes the feedthrough assembly of any one of examples 1-7, wherein the first surface of the first ledge has a height, and a ratio of the height of the first surface of the first ledge to the width of the base of the reservoir falls within a range of 0.45 to 0.75.

Example 9 includes the feedthrough assembly of any one of examples 1-8, wherein a measure of an angle at which the first surface and the second surface of at least one of the first and second ledges meet is selected in order to avoid wetting of the gold beyond the first surface of the second ledge.

Example 10 includes the feedthrough assembly of any one of examples 1-9, wherein a height of the first surface of the first ledge is selected in order to avoid wetting of the gold beyond the first surface of the second ledge.

Example 11 includes the feedthrough assembly of any one of examples 1-10, wherein a width of the second surface of the first ledge is selected in order to avoid wetting of the gold beyond the first surface of the second ledge.

Example 12 includes the feedthrough assembly of any one of examples 1-11, wherein a height of the first surface of the first ledge is less than a height of the preform of the braze material.

Example 13 includes the feedthrough assembly of any one of examples 1-12, wherein a height of the preform is selected in order for the preform, when placed in the base of the reservoir, to be located below an upper surface of the insulator.

Example 14 includes the feedthrough assembly of any one of examples 1-13, wherein the ferrule comprises titanium and the braze material comprises gold.

Example 15 includes the feedthrough assembly of any one of examples 1-14, in combination with a housing and a header attached to the housing, and in an implantable medical device.

Example 16 includes a feedthrough assembly, including: at least one electrically conductive member; an electrical insulator disposed about the at least one conductive member; and a ferrule comprising titanium and disposed about the insulator and having an outer surface and a first aperture defined by an inner surface, wherein the first aperture is sized and shaped to include a reservoir for a braze material comprising gold, the reservoir including a base, the base having a width sized to accommodate a preform of the braze material, and a first ledge and a second ledge formed by the inner surface, each ledge having a first surface facing inwardly toward the insulator and a second surface facing upwardly, wherein the first surface of a first ledge of the at least two ledges extends upwardly from the base of the reservoir, the second surface of the first ledge meets the first surface of the first ledge orthogonally and extends outwardly away from the insulator, the first surface of a second ledge extends upwardly from the second surface of the first ledge, and the second surface of the second ledge meets the first surface of the second ledge orthogonally and extends outwardly away from the insulator, and wherein the first surface of the first ledge has a height, and a ratio of the height of the first surface of the first ledge to the width of the base of the reservoir falls within a range of 0.45 to 0.75, further wherein the height of the first surface of the first ledge is less than a height of the preform, and the height of the preform is selected in order for the preform, when placed in the base of the reservoir, to be located below an upper surface of the insulator; wherein the insulator is separated from the ferrule by a first braze region that is connected to the base of the reservoir, and the insulator is separated from the conductive member by a second braze region, each braze region is configured to be filled with the braze material that hermetically seals the feedthrough assembly.

Example 17 includes a method for making a feedthrough assembly, the feedthrough assembly, the method including: providing a ferrule having an outer surface and a first aperture defined by an inner surface, wherein the first aperture is sized and shaped to include a reservoir for a braze material, the reservoir including a base, the base having a width sized to accommodate a first preform of the braze material, and at least two ledges formed by the inner surface, each ledge having a first surface facing inwardly toward the insulator and a second surface facing upwardly, and a first ledge of the at least two ledges is located radially inward toward the insulator from a second ledge; providing an electrical insulator in the first aperture, the insulator having a first surface separated from the inner surface of the ferrule by the reservoir and by a first braze region, and a second surface defining a second aperture; providing an electrically conductive element in the second aperture, the conductive element is spaced from the insulator by a second braze region; providing the first preform comprising the braze material to the base of the reservoir and a second preform adjacent the second braze region; and heating the assembly to melt the first and second preforms and braze the ferrule to the insulator in the first braze region and to braze the conductive element to the insulator in the second braze region.

Example 18 includes the method of example 17, wherein prior to providing the ferrule: selecting a measure of an angle at which the first surface and the second surface of the first and second ledges of the inner surface of the ferrule meet; and selecting a height of the first surface of the first ledge of the inner surface of the ferrule, in order to avoid wetting of the braze material, during heating the assembly, beyond the first surface of the second ledge.

Example 19 includes the method of any one of examples 17-18, wherein prior to providing the ferrule: selecting the angles at which the first surface and the second surface of each of the at least two ledges meet as orthogonally.

Example 20 includes the method of any one of examples 17-19, wherein prior to providing the ferrule: selecting a height of the first surface of the first ledge such that a ratio of the height of the first surface of the first ledge to the width of the base of the reservoir falls within a range of 0.45 to 0.75.

What is claimed is:

1. A feedthrough assembly, comprising:
   at least one electrically conductive member;
   an electrical insulator disposed about the at least one conductive member; and
   a ferrule disposed about the insulator and having an outer surface and a first aperture defined by an inner surface, wherein the first aperture is sized and shaped to include a reservoir for a braze material, the reservoir including a base, the base having a width sized to accommodate a preform of the braze material, and at least two ledges separate from the base, formed by the inner surface, each ledge having a first surface facing inwardly toward the insulator and a second surface facing upwardly;
   wherein the insulator is separated from the ferrule by a first braze region that is connected to the base of the reservoir, and the insulator is separated from the conductive member by a second braze region, each braze region is configured to be filled with the braze material that hermetically seals the feedthrough assembly.

2. The feedthrough assembly of claim 1, wherein the ferrule comprises titanium and the braze material comprises gold, and a first ledge of the at least two ledges is located radially inward toward the insulator from a second ledge, and a measure of an angle at which the first surface and the second surface of each of the first and second ledges meet and a height of the first surface of the first ledge are selected in order to avoid wetting of the gold beyond the first surface of the second ledge.

3. The feedthrough assembly of claim 1, wherein the first surface and the second surface of each of the at least two ledges meet orthogonally.

4. The feedthrough assembly of claim 3, wherein the first surface of a first ledge of the at least two ledges extends upwardly from the base of the reservoir, the second surface of the first ledge meets the first surface of the first ledge orthogonally and extends outwardly away from the insulator, the first surface of a second ledge extends upwardly from the second surface of the first ledge, and the second surface of the second ledge meets the first surface of the second ledge orthogonally and extends outwardly away from the insulator.

5. The feedthrough assembly of claim 1, wherein the reservoir concentrically surrounds the insulator and the at least two ledges extend around the insulator.

6. The feedthrough assembly of claim 1, wherein the feedthrough assembly has a longitudinal axis and the at least two ledges are offset from each other along the longitudinal axis.

7. The feedthrough assembly of claim 1, wherein a first ledge of the at least two ledges is located radially inward toward the insulator from a second ledge.

8. The feedthrough assembly of claim 7, wherein the first surface of the first ledge has a height, and a ratio of the height of the first surface of the first ledge to the width of the base of the reservoir falls within a range of 0.45 to 0.75.

9. The feedthrough assembly of claim 7, wherein a measure of an angle at which the first surface and the second surface of at least one of the first and second ledges meet is selected in order to avoid wetting of the gold beyond the first surface of the second ledge.

10. The feedthrough assembly of claim 7, wherein a height of the first surface of the first ledge is selected in order to avoid wetting of the gold beyond the first surface of the second ledge.

11. The feedthrough assembly of claim 7, wherein a width of the second surface of the first ledge is selected in order to avoid wetting of the gold beyond the first surface of the second ledge.

12. The feedthrough assembly of claim 7, wherein a height of the first surface of the first ledge is less than a height of the preform of the braze material.

13. The feedthrough assembly of claim 1, wherein a height of the preform is selected in order for the preform, when placed in the base of the reservoir, to be located below an upper surface of the insulator.

14. The feedthrough assembly of claim 1, wherein the ferrule comprises titanium and the braze material comprises gold.

15. The feedthrough assembly of claim 1, in combination with a housing and a header attached to the housing, and in an implantable medical device.

16. A feedthrough assembly, comprising:
at least one electrically conductive member;
an electrical insulator disposed about the at least one conductive member; and
a ferrule comprising titanium and disposed about the insulator and having an outer surface and a first aperture defined by an inner surface, wherein the first aperture is sized and shaped to include a reservoir for a braze material comprising gold, the reservoir including a base, the base having a width sized to accommodate a preform of the braze material, and a first ledge and a second ledge separate from the base, formed by the inner surface, each ledge having a first surface facing inwardly toward the insulator and a second surface facing upwardly, wherein the first surface of a first ledge of the at least two ledges extends upwardly from the base of the reservoir, the second surface of the first ledge meets the first surface of the first ledge orthogonally and extends outwardly away from the insulator, the first surface of a second ledge extends upwardly from the second surface of the first ledge, and the second surface of the second ledge meets the first surface of the second ledge orthogonally and extends outwardly away from the insulator, and wherein the first surface of the first ledge has a height, and a ratio of the height of the first surface of the first ledge to the width of the base of the reservoir falls within a range of 0.45 to 0.75, further wherein the height of the first surface of the first ledge is less than a height of the preform, and the height of the preform is selected in order for the preform, when placed in the base of the reservoir, to be located below an upper surface of the insulator;
wherein the insulator is separated from the ferrule by a first braze region that is connected to the base of the reservoir, and the insulator is separated from the conductive member by a second braze region, each braze region is configured to be filled with the braze material that hermetically seals the feedthrough assembly.

17. A method for making a feedthrough assembly, the method comprising:
providing a ferrule having an outer surface and a first aperture defined by an inner surface, wherein the first aperture is sized and shaped to include a reservoir for a braze material, the reservoir including a base, the base having a width sized to accommodate a first preform of the braze material, and at least two ledges separate from the base, formed by the inner surface, each ledge having a first surface facing inwardly toward the insulator and a second surface facing upwardly, and a first ledge of the at least two ledges is located radially inward toward the insulator from a second ledge;
providing an electrical insulator in the first aperture, the insulator having a first surface separated from the inner surface of the ferrule by the reservoir and by a first braze region, and a second surface defining a second aperture;
providing an electrically conductive element in the second aperture, the conductive element is spaced from the insulator by a second braze region;
providing the first preform comprising the braze material to the base of the reservoir and a second preform adjacent the second braze region; and
heating the assembly to melt the first and second preforms and braze the ferrule to the insulator in the first braze region and to braze the conductive element to the insulator in the second braze region.

18. The method of claim 17, wherein prior to providing the ferrule:
selecting a measure of an angle at which the first surface and the second surface of the first and second ledges of the inner surface of the ferrule meet; and
selecting a height of the first surface of the first ledge of the inner surface of the ferrule, in order to avoid wetting of the braze material, during heating the assembly, beyond the first surface of the second ledge.

19. The method of claim 17, wherein prior to providing the ferrule:
selecting the angles at which the first surface and the second surface of each of the at least two ledges meet as orthogonally.

20. The method of claim 17, wherein prior to providing the ferrule:
selecting a height of the first surface of the first ledge such that a ratio of the height of the first surface of the first ledge to the width of the base of the reservoir falls within a range of 0.45 to 0.75.

* * * * *